United States Patent
Prasad et al.

(10) Patent No.: US 10,842,900 B2
(45) Date of Patent: Nov. 24, 2020

(54) AIR TREATMENT ARTICLE

(71) Applicants: Dow Global Technologies LLC, Midland, MI (US); Rohm and Haas Company, Collegeville, PA (US)

(72) Inventors: Vikram Prasad, Midland, MI (US); Michelle Gallagher, Cherry Hill, NJ (US); Chaofang Yue, Dublin, CA (US)

(73) Assignees: Dow Global Technologies LLC, Midland, MI (US); Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 16/333,830

(22) PCT Filed: Sep. 14, 2017

(86) PCT No.: PCT/US2017/051450
§ 371 (c)(1),
(2) Date: Mar. 15, 2019

(87) PCT Pub. No.: WO2018/063808
PCT Pub. Date: Apr. 5, 2018

(65) Prior Publication Data
US 2019/0247530 A1 Aug. 15, 2019

Related U.S. Application Data

(60) Provisional application No. 62/400,781, filed on Sep. 28, 2016.

(51) Int. Cl.
| | |
|---|---|
| *A61L 9/014* | (2006.01) |
| *B01D 53/12* | (2006.01) |
| *B01D 53/22* | (2006.01) |
| *B01D 53/81* | (2006.01) |
| *A61L 9/01* | (2006.01) |
| *B01D 67/00* | (2006.01) |
| *B01D 53/04* | (2006.01) |
| *B01D 69/02* | (2006.01) |
| *B01D 69/08* | (2006.01) |

(52) U.S. Cl.
CPC ............ *A61L 9/014* (2013.01); *A61L 9/01* (2013.01); *B01D 53/04* (2013.01); *B01D 53/12* (2013.01); *B01D 53/228* (2013.01); *B01D 53/81* (2013.01); *B01D 67/0004* (2013.01); *B01D 69/02* (2013.01); *B01D 69/08* (2013.01); *A61L 2209/14* (2013.01); *A61L 2209/21* (2013.01); *A61L 2209/22* (2013.01); *B01D 2053/224* (2013.01); *B01D 2253/202* (2013.01); *B01D 2253/25* (2013.01); *B01D 2257/40* (2013.01); *B01D 2257/708* (2013.01); *B01D 2257/7022* (2013.01); *B01D 2257/90* (2013.01); *B01D 2258/06* (2013.01); *B01D 2259/4508* (2013.01); *B01D 2325/12* (2013.01)

(58) Field of Classification Search
None
See application file for complete search history.

(56) References Cited

U.S. PATENT DOCUMENTS

| | | |
|---|---|---|
| 3,798,876 A | 3/1974 | Kennedy |
| 4,863,494 A | 9/1989 | Hayes |
| 7,531,471 B2 | 5/2009 | Quincy, III |
| 2004/0009872 A1 | 1/2004 | Cohen et al. |
| 2009/0048365 A1 | 2/2009 | Brain et al. |
| 2009/0162558 A1 | 6/2009 | Bardman et al. |
| 2009/0318287 A1 | 12/2009 | MacDonald |
| 2016/0028511 A1 | 1/2016 | Papasakellariou et al. |
| 2016/0220952 A1 | 8/2016 | Whitehead et al. |

FOREIGN PATENT DOCUMENTS

| | | |
|---|---|---|
| AU | 728430 B2 | 1/2001 |
| DE | 10156717 A1 | 5/2003 |
| DE | 202008016507 U1 | 12/2009 |
| JP | H02300315 A | 12/1990 |
| WO | 2000040224 A1 | 7/2000 |
| WO | 2015181029 A1 | 12/2015 |

*Primary Examiner* — Walter D. Griffin
*Assistant Examiner* — Jelitza M Perez
(74) *Attorney, Agent, or Firm* — Thomas S. Deibert

(57) ABSTRACT

An air treatment article is provided, comprising: a semipermeable barrier and a plurality of multi-staged non-film forming polymer abatement particles having a core polymer and at least one shell polymer; wherein the core polymer accounts for 1 to 25 wt % of the weight of the non-film forming polymer abatement particles; wherein the semipermeable barrier is disposed between an air atmosphere and the non-film forming polymer abatement particles; wherein the semipermeable barrier impedes passage therethrough by the non-film forming polymer abatement particles; wherein the semipermeable barrier permits passage therethrough by a for-treatment air containing a contaminant such that the for-treatment air can make contact with the non-film forming polymer abatement particles; wherein the non-film forming polymer abatement particles have an affinity for the contaminant.

9 Claims, No Drawings

AIR TREATMENT ARTICLE

The present invention relates to an air treatment article. In particular, the present invention relates to an air treatment article, comprising: a semipermeable barrier and a plurality of multi-staged non-film forming polymer abatement particles having a core polymer and at least one shell polymer; wherein the core polymer accounts for 1 to 25 wt % of the weight of the non-film forming polymer abatement particles; wherein the semipermeable barrier is disposed between an air atmosphere and the non-film forming polymer abatement particles; wherein the semipermeable barrier impedes passage therethrough by the non-film forming polymer abatement particles; wherein the semipermeable barrier permits passage therethrough by a for-treatment air containing a contaminant such that the for-treatment air can make contact with the non-film forming polymer abatement particles; wherein the non-film forming polymer abatement particles have an affinity for the contaminant.

Air contamination in indoor spaces can take many forms including, for example, particulate matter (such as smoke and soot), biological agents (such as mold) and volatile organic compounds (VOCs). Some of the more common VOCs found in indoor spaces include benzene, toluene, acetaldehyde and trichloroethylene. Some VOCs are microbial in origin and are termed as microbial volatile organic compounds (mVOCs). Common examples include 3-octanone, 2-octen-1-ol, 1-butanol and 2-methyl-1-propanol.

Exposure to VOCs and mVOCs contaminants in indoor environments has been linked to multiple adverse health effects. Accordingly, the abatement of these volatiles can lead to improvement in public health and better quality of life. Treatment of indoor air to remove VOCs/mVOCs typically involves a combination of approaches such as removal of the source of the pollution, improving air distribution and treatment of the indoor air itself. One of the ways of treating air involves adsorption, wherein the contaminants are adsorbed on to materials such as activated carbon and zeolites. However, it is unclear whether these materials absorb VOCs/mVOCs effectively.

One method for air pollution abatement is disclosed by Kennedy in U.S. Pat. No. 3,798,876. Kennedy discloses a method of air pollution abatement substantially precluding dissipation into the ambient air of the vaporized organic compounds emitted by industrial plants, which comprises: (a) diverting industrial organic vapors from such plants into a mass or bed of macroreticular water insoluble cross linked polymer composed of 10 to 100 wt % of a polyvinyl methacrylate containing at least three methacrylate groups, wherein the balance of the polymer to make a 100 wt % is a monoethylenically or diethylenically unsaturated comonomer or derivatives of said polymer containing a group selected from the class consisting of sulfonic acid, amine oxide, quaternary ammonium amine, sulfoxide, amide, and ketone functionality; which polymer has a surface area of at least 10 to 1,000 m$^2$/g, a porosity of at least 25% ranging up to 85% and pores of an average diameter of at least 20 angstroms ranging up to 20,000 angstroms; (b) contacting the loaded polymer with a reagent fluid to release substantially all of the adsorbed organics; and (c) directing the desorbed organics to a disposal other than by atmospheric discharge.

Another air purification apparatus including high temperature regenerated adsorbent particles is disclosed by Hayes in U.S. Pat. No. 4,863,494. Hayes discloses a method of filtering volatile organic compounds from an air stream wherein the method comprises the steps of: (a) forming a fluid bed of beads of substantially pure divinyl benzene wherein the beads have a surface area of about 700 m$^2$/g or greater, a pore volume in the range of about 1.8 to 2.24 cc/g, at least 72% pores wherein more than half the pores are in the range of about 30 to about 95 angstroms; (b) directing a volatile organic compound in fluid flow through said bed while organic compounds are adsorbed out of the fluid flow; and (c) periodically regenerating the fluid bed by passing a purged fluid therethrough at temperatures elevated above ambient temperature but limited to not more than about 290° C.

Notwithstanding, there remains a need for improved air treatment articles designed to facilitate the effective removal of airborne contaminants (particularly volatile odoriferous contaminants). In particular, there remains a need for improved air treatment articles designed for removing airborne contaminants from confined spaces (e.g., dwelling places; passenger cabins in automobiles, buses, trains, aircraft; etc.).

The present invention provides an air treatment article, comprising: a semipermeable barrier and a plurality of non-film forming polymer abatement particles; wherein the non-film forming polymer abatement particles provided are multi-staged particles comprising: a core polymer and at least one shell polymer; wherein the core polymer accounts for 1 to 25 wt % of the non-film forming polymer abatement particles; wherein the core polymer comprises, as polymerized monomer units, 50 to 100 wt %, based on the weight of the core polymer, of at least one type of monoethylenically unsaturated core monomer containing a single carboxylic acid group; wherein the at least one shell polymer comprises, as polymerized monomer units: 10 to 50 wt %, based on the weight of the at least one shell polymer, of at least one type of multiethylenically unsaturated shell monomer; and 50 to 90 wt %, based on the weight of the at least one shell polymer, of at least one type of monoethylenically unsaturated shell monomer; wherein the non-film forming polymer abatement particles provided each contain a central void, wherein the non-film forming polymer abatement particles provided have an average void fraction of 1 to 70 vol %; wherein the semipermeable barrier is disposed between an air atmosphere and the non-film forming polymer abatement particles; wherein the semipermeable barrier impedes passage therethrough by the non-film forming polymer abatement particles; wherein the semipermeable barrier permits passage therethrough by a for-treatment air containing a contaminant such that the for-treatment air can make contact with the non-film forming polymer abatement particles; wherein the non-film forming polymer abatement particles have an affinity for the contaminant, wherein the contaminant comprises at least one of acetaldehyde, d-limonene, an aromatic, a pyridine, a pyrazine, 1-octen-3-ol, 3-methylfuran, 2-pentanol, 2-hexanone, 2-heptanone, 3-octanone, 3-octanol, trans-2-octen-1-ol, cis-2-octen-1-ol, 1-octene, 2-pentanone, 2-nonanone, borneol, geosmin, 1-butanol, 3-methyl-1-butanol, 3-methyl-2-butanol and thujopsene.

The present invention also provides an air treatment article, comprising: a semipermeable barrier and a plurality of non-film forming polymer abatement particles; wherein the non-film forming polymer abatement particles provided are multi-staged particles comprising: a core polymer and at least one shell polymer; wherein the core polymer accounts for 1 to 25 wt % of the non-film forming polymer abatement particles; wherein the core polymer comprises, as polymerized monomer units, 50 to 100 wt %, based on the weight of the core polymer, of at least one type of monoethylenically unsaturated core monomer containing a single carboxylic acid group; wherein the at least one shell polymer comprises, as polymerized monomer units: 10 to 50 wt %, based on the weight of the at least one shell polymer, of at least one type of multiethylenically unsaturated shell monomer; and 50 to 90 wt %, based on the weight of the at least one shell polymer, of at least one type of monoethylenically unsaturated shell monomer; wherein the non-film forming polymer abatement particles provided each contain a central void, wherein the non-film forming polymer abatement particles provided have an average void fraction of 1 to 70 vol %; wherein the semipermeable barrier is disposed between an air atmosphere and the non-film forming polymer abatement particles; wherein the semipermeable barrier impedes passage therethrough by the non-film forming polymer abatement particles; wherein the semipermeable barrier permits passage therethrough by a for-treatment air containing a contaminant such that the for-treatment air can make contact with the non-film forming polymer abatement particles; wherein the non-film forming polymer abatement particles have an affinity for the contaminant, wherein the contaminant comprises at least one of acetaldehyde, d-limonene, an aromatic, a pyridine, a pyrazine, 1-octen-3-ol, 3-methylfuran, 2-pentanol, 2-hexanone, 2-heptanone, 3-octanone, 3-octanol, trans-2-octen-1-ol, cis-2-octen-1-ol, 1-octene, 2-pentanone, 2-nonanone, borneol, geosmin, 1-butanol, 3-methyl-1-butanol, 3-methyl-2-butanol and thujopsene.

DETAILED DESCRIPTION

We have surprisingly found that hollow core non-film forming styrene/acrylic polymer abatement particles have exceptional contaminant scavenging ability for extracting airborne contaminants from indoor air, in particular, the ability to extract odoriferous volatile contaminants (both VOCs and mVOCs), for example, the odoriferous volatile contaminants associated with cigarette smoke.

As used herein, all percentages referred to will be expressed in weight percent (wt %), based on the weight of polymer or composition involved, unless specified otherwise.

The term "fiber" as used herein and in the appended claims refers to a unit of matter capable of being spun into a yarn or made into a fabric by bonding or by interlacing in a variety of ways including, for example, weaving, knitting, braiding, felting, twisting or webbing; and which is the basic structural element of textile products.

The term "yarn" as used herein and in the appended claims refers to a strand of textile fiber in a form suitable for weaving, knitting, braiding, felting, twisting, webbing, or otherwise fabricating into a fabric.

The term "fabric" as used herein and in the appended claims refers to any material woven, knitted, felted, or otherwise produced from, or in combination with, any natural or manufactured fiber, yarn, or substitute therefor.

The term "sheath/hollow cavity fiber configuration" or "sheath/core fiber configuration" as used herein and in the appended claims encompass multicomponent fiber concentric sheath/cavity configurations and eccentric sheath/cavity configurations.

The term "side-by-side configuration" as used herein and in the appended claims refers to an extension of a multicomponent fiber eccentric sheath/cavity configuration in which both component polymers of the multicomponent fiber occupy a portion of the multicomponent fiber's surface.

As used herein, the term "(meth)acrylic" refers to either (or both) acrylic acid and methacrylic acid.

As used herein, the term "alkyl (meth)acrylate" refers to either (or both) the corresponding alkyl acrylate or alkyl methacrylate.

As used herein, the term "copolymer" or "copolymer material" refers to polymer compositions containing monomer residues of at least two different types of monomer.

As used herein, the term "shell" refers to the particle shell polymer composition (not including the particle core polymer) prepared from single or multistage polymerizations.

The term "polymer" as used herein and in the appended claims refers to a compound prepared by polymerizing monomers, whether of the same or a different type. The generic term "polymer" includes the terms "homopolymer" and "copolymer."

Preferably, the air treatment article of the present invention, comprises: a semipermeable barrier and a plurality of non-film forming polymer abatement particles; wherein the non-film forming polymer abatement particles are multi-staged particles comprising: a core polymer and at least one shell polymer; wherein the core polymer accounts for 1 to 25 wt % (more preferably, 2 to 12 wt %) of the weight of the non-film forming polymer abatement particles; wherein the core polymer comprises, as polymerized monomer units, 50 to 100 wt % (preferably, 75 to 100 wt %; more preferably, 90 to 100 wt %; still more preferably, 95 to 100 wt %; most preferably, 99 to 100 wt %), based on the weight of the core polymer, of at least one type of monoethylenically unsaturated core monomer containing a single carboxylic acid group; wherein the at least one shell polymer comprises, as polymerized monomer units: 10 to 50 wt % (preferably, 15 to 35 wt %; more preferably, 15 to 30 wt %; most preferably, 20 to 30 wt %), based on the weight of the at least one shell polymer, of at least one type of multiethylenically unsaturated shell monomer (preferably, wherein the at least one type of multiethylenically unsaturated shell monomer is divinyl benzene); and 50 to 90 wt % (preferably, 65 to 85 wt %; more preferably, 70 to 85 wt %; most preferably, 70 to 80 wt %), based on the weight of the at least one shell polymer, of at least one type of monoethylenically unsaturated shell monomer; wherein the non-film forming polymer abatement particles each contain a central void, wherein the non-film forming polymer abatement particles have an average void fraction of 1 to 70 vol % (more preferably, 5 to 50 vol %, still more preferably, 10 to 40 vol %; most preferably, 20 to 35 vol %); wherein the semipermeable barrier is disposed between an air atmosphere and the non-film forming polymer abatement particles; wherein the semipermeable barrier impedes passage therethrough by the non-film forming polymer abatement particles; wherein the semipermeable barrier permits passage therethrough by a for-treatment air containing a contaminant such that the for-treatment air can make contact with the non-film forming polymer abatement particles; wherein the non-film forming polymer abatement particles have an affinity for the contaminant (preferably such that, upon contact with the for-treatment air, the contaminant is extracted from the for-treatment air to produce a treated air depleted in the contaminant); wherein the contaminant comprises at least one of acetaldehyde, d-limonene, an aromatic (e.g., benzene, toluene, ethylbenzene, xylene, styrene, trimethylbenzene, propylbenzene), a pyridine (e.g., pyridine, methylpyridine, ethylpyridine, propylpyridine, vinylpyridine), a pyrazine (e.g., pyrazine, methylpyrazine, dimethylpyrazine), 1-octen-3-ol, 3-methylfuran, 2-pentanol, 2-hexanone, 2-heptanone, 3-octanone, 3-octanol, trans-2-octen-1-ol, cis-2-octen-1-ol, 1-octene, 2-pentanone, 2-nonanone, borneol, geosmin, 1-butanol, 3-methyl-1-butanol, 3-methyl-2-butanol and thujopsene (preferably, wherein the contaminant comprises at least one of d-limonene, an aromatic, 3-octanone and 1-butanol; more preferably, wherein the contaminant comprises at least one of d-limonene, ethylbenzene and 3-octanone; most preferably, wherein the contaminant comprises 3-octanone).

Preferably, the non-film forming polymer abatement particles used in the air treatment article of the present invention each comprise a core polymer and at least one shell polymer. More preferably, the non-film forming polymer abatement particles used in the air treatment article of the present invention each comprise a multi-staged particle comprising a core polymer and at least one shell polymer; wherein the core polymer accounts for an average of 1 to 25 wt % (more preferably, 2 to 12 wt %) of each particle in the plurality of the non-film forming polymer abatement particles.

Preferably, the core polymer of the non-film forming polymer abatement particles includes, as polymerized monomer units, 50 to 100 wt %, based on the weight of the core polymer, of at least one type of monoethylenically unsaturated core monomer containing a single carboxylic acid group. More preferably, the core polymer of the non-film forming polymer abatement particles includes, as polymerized monomer units, 75 to 100 wt %, based on the weight of the core polymer, of at least one type of monoethylenically unsaturated core monomer containing a single carboxylic acid group. Still more preferably, the core polymer of the non-film forming polymer abatement particles includes, as polymerized monomer units, 90 to 100 wt %, based on the weight of the core polymer, of at least one type of monoethylenically unsaturated core monomer containing a single carboxylic acid group. Yet still more preferably, the core polymer of the non-film forming polymer abatement particles includes, as polymerized monomer units, 95 to 100 wt %, based on the weight of the core polymer, of at least one type of monoethylenically unsaturated core monomer containing a single carboxylic acid group. Most preferably, the core polymer of the non-film forming polymer abatement particles includes, as polymerized monomer units, 99 to 100 wt %, based on the weight of the core polymer, of at least one type of monoethylenically unsaturated core monomer containing a single carboxylic acid group.

Preferably, the core polymer is obtained by the emulsion homopolymerization of the monoethylenically unsaturated core monomer containing a single carboxylic acid group or by copolymerization of at least two different types of monoethylenically unsaturated core monomers containing a single carboxylic acid group.

Preferably, the monoethylenically unsaturated core monomer containing a single carboxylic acid group is selected from the group of core monomers consisting of acrylic acid, methacrylic acid, (meth)acryloxypropionic acid, crotonic acid, monomethyl maleate, monomethyl fumarate, and monomethyl itaconate. More preferably, the monoethylenically unsaturated core monomer containing a single carboxylic acid is selected from the group of core monomers consisting of acrylic acid and methacrylic acid. Most preferably, the monoethylenically unsaturated core monomer containing a single carboxylic acid is a mixture of acrylic acid monomer and methacrylic acid monomer.

Preferably, the core polymer contains, as polymerized monomer units, <1 wt %, based on the weight of the core polymer, of multiethylenically unsaturated core monomer. More preferably, the core polymer contains, as polymerized monomer units, <0.1 wt %, based on the weight of the core polymer, of multiethylenically unsaturated core monomer. Still more preferably, the core polymer contains, as polymerized monomer units, <0.01 wt %, based on the weight of the core polymer, of multiethylenically unsaturated core monomer. Most preferably, the core polymer contains, as polymerized monomer units, < the detectable limit of multiethylenically unsaturated core monomer.

Preferably, the types of monomer used in the emulsion polymerization to form the shell polymer of the plurality of non-film forming polymer abatement particles are selected from the group consisting of non-ionic ethylenically unsaturated monomers.

Preferably, the types of monomer used in the emulsion polymerization to form the shell polymer of the plurality of non-film forming polymer abatement particles, include 10 to 50 wt % (preferably, 15 to 35 wt %; more preferably, 15 to 30 wt %; most preferably, 20 to 30 wt %), based on the weight of the shell polymer, of at least one type of multiethylenically unsaturated shell monomer; and 50 to 90 wt % (preferably, 65 to 85 wt %; more preferably, 70 to 85 wt %; most preferably, 70 to 80 wt %), based on the weight of the shell polymer, of at least one type of monoethylenically unsaturated shell monomer.

Preferably, the at least one multiethylenically unsaturated shell monomer used to form the shell polymer include poly vinylic monomers consisting of at least one of diethyleneglycol divinyl ether, divinyl benzene, divinyl ketone, divinyl pyridine, divinyl sulfide, divinyl sulfone, divinyl toluene, divinyl xylene. More preferably, the at least one multiethylenically unsaturated shell monomer used to form the shell polymer includes divinyl benzene. Most preferably, the at least one multiethylenically unsaturated shell monomer used to form the shell polymer is divinyl benzene.

Preferably, the shell polymer of the plurality of non-film forming latex particles comprises, as polymerized monomer units, 10 to 50 wt % (preferably, 15 to 35 wt %; more preferably, 15 to 30 wt %; most preferably, 20 to 30 wt %), based on the weight of the shell polymer, of at least one type of multiethylenically unsaturated shell monomer selected from the group consisting of diethyleneglycol divinyl ether, divinyl benzene, divinyl ketone, divinyl pyridine, divinyl sulfide, divinyl sulfone, divinyl toluene and divinyl xylene. More preferably, the shell polymer of the plurality of non-film forming latex particles comprises, as polymerized monomer units, 10 to 50 wt % (preferably, 15 to 35 wt %; more preferably, 15 to 30 wt %; most preferably, 20 to 30 wt %), based on the weight of the shell polymer, of at least one type of multiethylenically unsaturated shell monomer includes divinyl benzene. Most preferably, the shell polymer of the plurality of non-film forming latex particles comprises, as polymerized monomer units, 10 to 50 wt % (preferably, 15 to 35 wt %; more preferably, 15 to 30 wt %; most preferably, 20 to 30 wt %), based on the weight of the shell polymer, of divinyl benzene.

Preferably, the shell polymer of the plurality of non-film forming latex particles comprises, as polymerized monomer units, <10 wt %, based on the weight of the shell polymer, of tri or higher methacrylate monomers. More preferably, the shell polymer of the plurality of non-film forming latex particles comprises, as polymerized monomer units, <1 wt %, based on the weight of the shell polymer, of tri or higher methacrylate monomers. Still more preferably, the shell polymer of the plurality of non-film forming latex particles comprises, as polymerized monomer units, <0.1 wt %, based on the weight of the shell polymer, of tri or higher methacrylate monomers. Most preferably, the shell polymer of the plurality of non-film forming latex particles comprises, as polymerized monomer units, less than the detectable limit of tri or higher methacrylate monomers.

Preferably, the at least one monoethylenically unsaturated shell monomer used to form the shell polymer is selected from the group consisting monoethylenically unsaturated shell monomers containing at least one carboxylic acid group; monoethylenically unsaturated shell monomers containing at least one non-carboxylic acid group; and monoethylenically unsaturated vinyl aromatic shell monomers.

Preferred monoethylenically unsaturated shell monomers containing at least one carboxylic acid group include, for example, acrylic acid, methacrylic acid, acryloxypropionic acid, methacryloxypropionic acid, aconitic acid, crotonic acid, maleic acid (and derivatives such as corresponding anhydride, amides and esters), fumaric acid (and derivatives such as corresponding amides and esters), itaconic and citraconic acids (and derivatives such as corresponding anhydrides, amides and esters). More preferred monoethylenically unsaturated shell monomers containing at least one carboxylic acid group are methacrylic acid and $C_{1-4}$ alkyl (meth)acrylate. Most preferred monoethylenically unsaturated shell monomers containing at least one carboxylic acid group are methacrylic acid, methyl methacrylate and butyl methacrylate.

Preferably, the shell polymer of the plurality of non-film forming latex particles comprises, as polymerized monomer units, 50 to 90 wt % (more preferably, 10 to 80 wt %; still more preferably, 15 to 70 wt %; most preferably, 20 to 30 wt %), based on the weight of the shell polymer, of monoethylenically unsaturated shell monomers containing at least one carboxylic acid group selected from the group consisting of at least one of methacrylic acid, methyl acrylate, methyl methacrylate, ethyl acrylate, ethyl methacrylate, butyl acrylate, butyl methacrylate, isobutyl acrylate, isobutyl methacrylate, hydroxyethyl methacrylate, hydroxypropyl methacrylate, dimethylaminoethyl methacrylate. More preferably, the shell polymer of the plurality of non-film forming latex particles comprises, as polymerized monomer units, 50 to 90 wt % (more preferably, 10 to 80 wt %; still more preferably, 15 to 70 wt %; most preferably, 20 to 30 wt %), based on the weight of the shell polymer, of monoethylenically unsaturated shell monomers containing at least one carboxylic acid group selected from the group consisting of at least one of methacrylic acid, methyl methacrylate and butyl methacrylate. Most preferably, the shell polymer of the plurality of non-film forming latex particles includes, as polymerized monomer units, 50 to 90 wt % (more preferably, 10 to 80 wt %; still more preferably, 15 to 70 wt %; most preferably, 20 to 30 wt %), based on the weight of the shell polymer, of methacrylic acid, methyl methacrylate and butyl methacrylate.

Preferred monoethylenically unsaturated shell monomers containing at least one non-carboxylic acid group include, for example, allyl sulfonic acid, allylphosphonic acid, allyloxybenzene sulfonic acid, 2-acrylamido-2-methylpropanesulfonic acid, 2-hydroxy-3(2-propenyloxy) propanesulfonic acid, 2-methyl-2-propene-1-sulfonic acid, 2-methacrylamido-2-methyl-1-propane sulfonic acid, 3-methacrylamido-2-hydroxy-1-propanesulfonic acid, isopropenylphosphonic acid, vinyl phosphonic acid, styrene sulfonic acid, vinylsulfonic acid and the alkali metal and ammonium salts thereof. More preferably monoethylenically unsaturated shell monomers containing non-carboxylic acid are 2-acrylamido-2-methyl propanesulfonic acid, styrenesulfonic acid and the alkali metal salts thereof. Most preferred monoethylenically unsaturated shell monomer containing non-carboxylic acid is sodium styrene sulfonate.

Preferably, the shell polymer of the plurality of non-film forming latex particles comprises, as polymerized monomer units, 0 to 10 wt % (more preferably, 0.1 to 5 wt %; most preferably, 0.5 to 3 wt %), based on the weight of the shell polymer, of monoethylenically unsaturated shell monomers containing at least one non-carboxylic acid group selected from the group consisting of at least one of allyl sulfonic acid, allylphosphonic acid, allyloxybenzene sulfonic acid, 2-acrylamido-2-methylpropanesulfonic acid, 2-hydroxy-3 (2-propenyloxy) propanesulfonic acid, 2-methyl-2-propene-1-sulfonic acid, 2-methacrylamido-2-methyl-1-propane sulfonic acid, 3-methacrylamido-2-hydroxy-1-propanesulfonic acid, isopropenylphosphonic acid, vinyl phosphonic acid, styrene sulfonic acid, vinylsulfonic acid and the alkali metal and ammonium salts thereof. More preferably, the shell polymer of the plurality of non-film forming latex particles comprises, as polymerized monomer units, 0 to 10 wt % (more preferably, 0.1 to 5 wt %; most preferably, 0.5 to 3 wt %), based on the weight of the shell polymer, of monoethylenically unsaturated shell monomers containing at least one non-carboxylic acid group selected from the group consisting of at least one of 2-acrylamido-2-methyl propanesulfonic acid, styrenesulfonic acid and the alkali metal salts thereof. Most preferably, the shell polymer of the plurality of non-film forming latex particles comprises, as polymerized monomer units, 0 to 10 wt % (more preferably, 0.1 to 5 wt %; most preferably, 0.5 to 3 wt %), based on the weight of the shell polymer, of sodium styrene sulfonate.

Preferred monoethylenically unsaturated vinyl aromatic shell monomers include, for example, styrene, α-methylstyrene, vinyltoluene, alkyl-substituted styrene (e.g., ethylvinylbenzene and tert-butylstyrene) and halogenated styrenes. More preferred monoethylenically unsaturated vinyl aromatic shell monomers are selected from the group consisting of styrene, ethyl vinyl benzene and tert-butylstyrene. The most preferred monoethylenically unsaturated vinyl aromatic shell monomer is styrene.

Preferably, the shell polymer of the plurality of non-film forming latex particles comprises, as polymerized monomer units, 10 to 80 wt % (more preferably, 25 to 70 wt %; most preferably, 30 to 60 wt %), based on the weight of the shell polymer, of monoethylenically unsaturated vinyl aromatic shell monomers selected from the group consisting of styrene, α-methylstyrene, vinyltoluene, alkyl-substituted styrene (e.g., ethylvinylbenzene and tert-butylstyrene) and halogenated styrenes. More preferably, the shell polymer of the plurality of non-film forming latex particles comprises, as polymerized monomer units, 10 to 80 wt % (more preferably, 25 to 70 wt %; most preferably, 30 to 60 wt %), based on the weight of the shell polymer, of monoethylenically unsaturated vinyl aromatic shell monomers selected from the group consisting of styrene, ethyl vinyl benzene and tert-butylstyrene.

Most preferably, the shell polymer of the plurality of non-film forming latex particles comprises, as polymerized monomer units, 10 to 80 wt % (more preferably, 25 to 70 wt %; most preferably, 30 to 60 wt %), based on the weight of the shell polymer, of styrene.

Preferably, the monomers that comprise the shell polymer of the plurality of non-film forming polymer abatement particles are selected to provide a glass transition temperature ($T_g$) in at least one shell which is high enough to support the void within the latex particle. Preferably the $T_g$ of at least one shell is >50° C. (more preferably, >60° C.; most preferably, >70° C.), as measured by differential scanning calorimetry (DSC).

Preferably, the amount of polymer deposited to form the shell polymer is sufficient to provide the plurality of non-film forming polymer abatement particles with an average particle size of 50 to 1,000 nm, as measured using a Brookhaven BI-90 photon correlation spectrometer. More preferably, the amount of polymer deposited to form the shell polymer is sufficient to provide the plurality of non-film forming polymer abatement particles with an average particle size of 100 to 600 nm, as measured using a Brookhaven BI-90 photon correlation spectrometer. Still more preferably, the amount of polymer deposited to form the shell polymer is sufficient to provide the plurality of non-film forming polymer abatement particles with an average particle size of 200 to 500 nm, as measured using a Brookhaven BI-90 photon correlation spectrometer. Most preferably, the amount of polymer deposited to form the shell polymer is sufficient to provide the plurality of non-film forming polymer abatement particles with an average particle size of 300 to 400 nm, as measured using a Brookhaven BI-90 photon correlation spectrometer.

Preferably, each particle in the plurality of non-film forming polymer abatement particles contains a void. Preferably, the void contained by each particle in the plurality of the non-film forming polymer abatement particles is preferably formed through swelling of the core with an aqueous basic swellant that permeates the shell and expands the core. This expansion may involve partial merging of the outer periphery of the core into the pores of the inner periphery of the shell and also partial enlargement or bulging of the shell and the entire particle overall. When the swellant is removed by drying, the shrinkage of the core develops a microvoid, the extent of which depends on the resistance of the shell to restoration to its previous size. Suitable swelling agents for the core include, for example, ammonia, ammonium hydroxide, alkali metal hydroxides (such as sodium hydroxide), and volatile lower aliphatic amines (such as trimethylamine and triethylamine). The swelling step may occur during any of the multistage shell polymerization steps, between any of the staged polymerization steps, or at the end of the multistage polymerization process.

Preferably, each particle in the plurality of non-film forming polymer abatement particles contains a void, wherein the average void fraction for the plurality of non-film forming polymer abatement particles provided is 1 to 70 vol %; more preferably, 5 to 50 vol %, still more preferably, 10 to 40 vol %; most preferably, 20 to 35 vol %. The void fraction is determined by comparing the volume occupied by a plurality of non-film forming polymer abatement particles after compaction from a dilute dispersion in a centrifuge to the volume of an equivalent population of non-voided polymer abatement particles having the same composition.

Preferably, the non-film forming polymer abatement particles are hollow core polymer abatement particles which each contain a single central void.

Preferably, the non-film forming polymer abatement particles contain, as polymerized monomer units, <10 wt % alkyl acrylate monomer. More preferably, the non-film forming polymer abatement particles contain, as polymerized monomer units, <1 wt % alkyl acrylate monomer. Still more preferably, the non-film forming polymer abatement particles contain, as polymerized monomer units, <0.1 wt % alkyl acrylate monomer. Most preferably, the non-film forming polymer abatement particles contain, as polymerized monomer units, less than the detectable limit of alkyl acrylate monomer.

Preferably, the non-film forming polymer particles provided in the air treatment method of the present invention contain <5 wt % water. More preferably, the non-film forming polymer particles provided in the air treatment method of the present invention contain <3 wt % water. Still more preferably, the non-film forming polymer particles provided in the air treatment method of the present invention contain <2 wt % water. Yet more preferably, the non-film forming polymer particles provided in the air treatment method of the present invention contain <1 wt % water. Most preferably, the non-film forming polymer particles provided in the air treatment method of the present invention are dry.

Preferably, the non-film forming polymer abatement particles have an affinity for a contaminant, wherein the contaminant is at least one of a volatile organic compound (VOC) and a microbial volatile organic compound (mVOC). More preferably, the non-film forming polymer abatement particles have an affinity for a contaminant, wherein the contaminant is an odoriferous contaminant. Still more preferably, the non-film forming polymer abatement particles have an affinity for a contaminant, wherein the contaminant includes at least one of acetaldehyde, d-limonene, an aromatic (e.g., benzene, toluene, ethylbenzene, xylene, styrene, trimethylbenzene, propylbenzene), a pyridine (e.g., pyridine, methylpyridine, ethylpyridine, propylpyridine, vinylpyridine), a pyrazine (e.g., pyrazine, methylpyrazine, dimethylpyrazine), 1-octen-3-ol, 3-methylfuran, 2-pentanol, 2-hexanone, 2-heptanone, 3-octanone, 3-octanol, trans-2-octen-1-ol, cis-2-octen-1-ol, 1-octene, 2-pentanone, 2-nonanone, borneol, geosmin, 1-butanol, 3-methyl-1-butanol, 3-methyl-2-butanol and thujopsene. Yet more preferably, the non-film forming polymer abatement particles have an affinity for at least one of acetaldehyde, d-limonene, an aromatic (e.g., benzene, toluene, ethylbenzene, xylene, styrene, trimethylbenzene, propylbenzene), a pyridine (e.g., pyridine, methylpyridine, ethylpyridine, propylpyridine, vinylpyridine), a pyrazine (e.g., pyrazine, methylpyrazine, dimethylpyrazine), 1-octen-3-ol, 3-methylfuran, 2-pentanol, 2-hexanone, 2-heptanone, 3-octanone, 3-octanol, trans-2-octen-1-ol, cis-2-octen-1-ol, 1-octene, 2-pentanone, 2-nonanone, borneol, geosmin, 1-butanol, 3-methyl-1-butanol, 3-methyl-2-butanol and thujopsene. Yet still more preferably, the non-film forming polymer abatement particles have an affinity for at least one of d-limonene, an aromatic, 3-octanone and 1-butanol; more preferably, wherein the contaminant comprises at least one of d-limonene, ethylbenzene and 3-octanone. Most preferably, the non-film forming polymer abatement particles have an affinity for 3-octanone. Preferably, the non-film forming polymer particle affinity for the contaminant is such that upon contact with a for-treatment air containing the contaminant, the contaminant will be extracted from the for-treatment air to produce a treated air depleted in the contaminant. It is believed that some of the key malodor contaminants present in cigarette smoke include acetaldehyde, aromatics, pyradines and pyrazines.

Preferably, the semipermeable barrier in the air treatment article of the present invention, impedes passage therethrough by the non-film forming polymer abatement particles and permits passage therethrough by the for-treatment air; and is disposed between an air atmosphere and the non-film forming polymer abatement particles. Preferably, the semipermeable barrier is selected from the group consisting of at least one of a screen, a mesh, a woven or non-woven substrate, an expanded metal and a membrane. Preferably, the semipermeable barrier comprises a plurality of fibers; and wherein the plurality of fibers form a thin woven or nonwoven mat.

Preferably, the semipermeable barrier in the air treatment article of the present invention comprises a multicomponent fiber, wherein the multicomponent fiber has a cross section selected from a sheath/hollow cavity configuration, a side by side configuration, a pie wedge configuration, a hollow pie wedge configuration, a segmented ribbon configuration, a segmented cross configuration, an islands-in-a-sea configuration, a tipped trilobal configuration and a conjugate configuration. More preferably, the multicomponent fiber has a cross section selected from a pie wedge configuration; a hollow pie wedge configuration; an islands-in-a-sea configuration and a sheath/hollow cavity configuration. Most preferably, the multicomponent fiber has a sheath/hollow cavity configuration. Preferably, one of the components of the multicomponent fiber include the non-film forming polymer abatement particles. Preferably, a component polymer composition used to form one of the components of the multicomponent fiber and the hollow core non-film forming polymer abatement particles are mixed before forming a multicomponent fiber. More preferably, a component polymer composition and the hollow core non-film forming polymer abatement particles are mixed during formation of the multicomponent fiber.

Preferably, the multicomponent fiber comprises at least two component polymer compositions and a plurality of hollow core non-film forming polymer abatement particles. More preferably, the at least two component polymer compositions have different chemical or physical properties. Most preferably, at least one of the component polymer compositions and the plurality of hollow core non-film forming polymer abatement particles are mixed.

Preferably, the semipermeable barrier in the air treatment article of the present invention comprises a multicomponent fiber, wherein the multicomponent fiber has a sheath/hollow cavity with a sheath and a hollow cavity; wherein the semipermeable barrier forms at least a portion of the sheath; and wherein the non-film forming polymer abatement particles are disposed (preferably, entrapped) within the hollow cavity.

Preferably, the multicomponent fiber used in the air treatment article of the present invention are prepared using known fiber forming techniques. Some of the most prevalent fiber forming techniques include, for example, extrusion, melt-blowing, wet spinning and dry spinning. In each of these methods, the fiber raw materials are softened into a flowable state and forced through a die and/or a spinneret to form the basic fiber, which is then typically manipulated mechanically to form the desired product fiber or multicomponent fiber. For example, the basic fiber may be stretched. In typical extrusion operations, component polymer compositions are first melted and then forced through a die and/or a spinneret to form the basic fiber, which may then be manipulated mechanically prior to cooling to form the desired product fiber of multicomponent fiber. In typical melt blowing operations, component polymer compositions containing thermoplastic materials are first melted and then blown through a die and/or spinneret to form the basic fiber, which is then cooled to provide the product fiber. In typical wet spinning operations, a solution of component polymer composition(s) and a solvent are forced through a die and/or spinneret to form the basic fiber, which may then be passed through a coagulating bath (e.g., a solution of sodium sulfate in water) to provide the product fiber. In typical dry spinning operations, a solution of component polymer composition(s) and a solvent are forced through a die and/or spinneret into air to form solid fibers. The fibers formed by these methods may, and often are, collected on a surface such as a belt to form a nonwoven web or are otherwise treated chemically or mechanically manipulated to change or enhance their physical or chemical properties.

Preferably, the multicomponent fiber further comprises at least one additive selected from fire retardants, colorants, pigments, dyes, tints, antistatic agents, brightening compounds, nucleating agents, antioxidants, UV stabilizers, fillers, softeners, lubricants, curing accelerators, hydrophilic materials, hydrophobic materials, anti-stain materials, anti-odor materials, antimicrobial agents, disinfecting agents.

Preferably, the air treatment article of the present invention further comprises an additional fiber. More preferably, the air treatment article of the present invention comprises an additional fiber and a multicomponent fiber having a sheath/hollow cavity fiber configuration with a sheath and a hollow cavity; wherein the semipermeable barrier forms at least a portion of the sheath; and wherein the non-film forming polymer abatement particles are disposed (preferably, entrapped) within the hollow cavity.

Preferably, the additional fiber is selected from the group consisting of natural fibers, synthetic fibers, inorganic fibers, combinations and blends thereof. The additional fiber includes fibers of any denier; multi- or mono-filaments; false twisted or twisted; multiple denier filaments into a single yarn through twisting and/or melting; multicomponent fibers exhibiting any type of cross-section, including, for example, sheath/core configurations, side by side configurations, pie wedge configurations, segmented ribbon configurations, segmented cross configurations, tipped trilobal configurations and conjugate configurations.

Natural fibers suitable for use in the air treatment article of the present invention include, for example, silk, cotton, wool, flax, fur, hair, cellulose, ramie, hemp, linen, wood pulp and combinations thereof.

Synthetic fibers suitable for use in the air treatment article of can be derived from materials including, for example polyolefins, such as polyethylene, polypropylene and polybutylene; halogenated polymers, such as polyvinyl chloride; polyaramids, such as poly-p-phenyleneteraphthalamid (e.g. Kevlar® fibers available from DuPont), poly-m-phenyleneteraphthalamid (e.g., Nomex® fibers available from DuPont); melamine and melamine derivatives (e.g., Basofil® fibers available from Basofil Fibers, LLC); polyesters, such as polyethylene terephthalate, polyester/polyethers; polyamides, such as nylon 6 and nylon 6,6; polyurethanes, such as Tecophilic® aliphatic thermoplastic polyurethanes available from Noveon; acetates; rayon acrylics; and combinations thereof.

Inorganic fibers suitable for use in the air treatment article of the present invention include, for example, fiberglass, boron fibers and rock wool.

Preferably, the air treatment article of the present invention is a multicomponent fiber having a sheath/hollow cavity fiber configuration with a sheath and a hollow cavity; wherein the semipermeable barrier forms at least a portion of the sheath; and wherein the non-film forming polymer abatement particles are disposed (preferably, entrapped) within the hollow cavity. More preferably, the air treatment article of the present invention is a multicomponent fiber having a sheath/hollow cavity fiber configuration with a sheath and a hollow cavity; wherein the semipermeable barrier forms at least a portion of the sheath; and wherein the non-film forming polymer abatement particles are disposed (preferably, entrapped) within the hollow cavity; wherein the air treatment article is a textile product incorporating a fabric, wherein the fabric incorporates the multicomponent fiber. Preferably, the fabric comprises 100 wt % (more preferably, ≤75 wt %; still more preferably, ≤50 wt %; most preferably, ≤25 wt %) of the multicomponent fiber of the present invention. Preferably, the fabric further comprises an additional fiber selected from the group consisting of cotton, wool, polyester, acrylic, nylon, silk, and combinations and blends thereof. Most preferably, the air treatment article of the present invention is a multicomponent fiber having a sheath/hollow cavity fiber configuration with a sheath and a hollow cavity; wherein the semipermeable barrier forms at least a portion of the sheath; and wherein the non-film forming polymer abatement particles are disposed (preferably, entrapped) within the hollow cavity; wherein the air treatment article is a textile product incorporating a fabric, wherein the fabric incorporates the multicomponent fiber; wherein the textile product is selected from the group consisting of apparel, upholstery, carpeting, wall coverings, bedding, towels, gloves, rugs, floor mats, drapery, napery, bar runners, awnings, automotive headliners and filters.

Preferably, the plurality of non-film forming polymer abatement particles in the air treatment article of the present invention are a free flowing powder. More preferably, the plurality of non-film forming polymer abatement particles are a free flowing powder, wherein the non-film forming polymer abatement particles are subjectable to fluidization upon contact with the for treatment air.

Preferably, the plurality of non-film forming polymer abatement particles in the air treatment article of the present invention are in a packed bed configuration. More preferably, the plurality of non-film forming polymer abatement particles in the air treatment article of the present invention are disposed between a plurality of semipermeable barriers.

Preferably, the plurality of non-film forming polymer abatement particles in the air treatment article of the present invention are packed together such that the non-film forming polymer abatement particles remain stationary to one another upon contact with the for treatment air. More preferably, the plurality of non-film forming polymer abatement particles in the air treatment article of the present invention are packed together such that the non-film forming polymer abatement particles remain stationary to one another upon contact with the for treatment air; wherein the semipermeable barrier of the air treatment article is folded over on itself forming a pocket (or a plurality of pockets); wherein the non-film forming polymer abatement particles are disposed within the pocket (or the plurality of pockets). The plurality of pockets can be formed through, for example, stacking of at least two semipermeable barriers or folding a semipermeable barrier. Preferably, the air treatment article comprises at least two semipermeable barriers, wherein the non-film forming polymer abatement particles are interposed between the semipermeable barriers.

Preferably, the air treatment article of the present invention is designed to be incorporated in an HVAC system for an interior space. More preferably, the air treatment article of the present invention is designed to engage an air vent assembly for attachment to an air vent register of an HVAC system for an interior space. Most preferably, the air treatment article of the present invention is designed to engage an air vent assembly for attachment to an air vent register of an HVAC system for an interior space; wherein the interior space is selected from an abode (e.g., a home, an apartment, a hotel room); an office; and a passenger cabin (e.g., automobile, bus, train, aircraft, boat).

Some embodiments of the present invention will now be described in detail in the following Examples.

Comparative Examples C1-C9 and Examples 1-4, 5a-5d and 6-9: Contaminant Abatement The following contaminant analyte abatement experiments were performed by equilibrium headspace GC-MS VOC analysis with an Agilent 6890GC with 5973 MS detector and a Perkin Elmer TurboMatrix 40 Trap Headspace Sampler using the following instrument parameters:

Column: Model No. J&W 122-7033 DB-Wax column (30 m×0.25 mm×0.5 m); constant flow mode; 11.37 psi nominal inlet pressure; 25 cm/sec average velocity; helium gas.

Inlet conditions: split mode; 200° C.; 11.36 psi; 0.2:1 split ratio; 0.2 mL/min split flow; 3.9 mL/min total flow.

Oven program: 40° C. initial temperature with a 5 min. hold; 20° C./min linear temperature ramp; 250° C. final temperature with a 9.0 min. hold; 24.50 min. total run time.

Mass detector: SCAN acquisition mode; 1494.1 resulting EM voltage; 28.0 low mass; 200.0 high mass; 150° C. quad temp.; 230° C. source temp.

Headspace autosampler parameters: 35° C. (equilibrium)/150° C. (bulk) oven temperature; 60° C. (equilibrium)/175° C. (bulk) needle temperature; 100° C. (equilibrium)/200° C. (bulk) transfer line temperature; 10 min. vial equilibrium time; 2.0 min pressurization time; 0.1 min. injection time; 35 min. GC cycle time; 25 psi carrier pressure; operating mode: constant; injection mode: time.

A set of standards of known concentrations were prepared for each of the contaminant analytes tested in tetrahydrofuran (THF). The standards were run under high temperature headspace conditions (150° C., 10 min.) to provide full liberation of the contaminant analytes into the headspace of 22 mL headspace vials. The weight concentrations were converted to ppm volume/volume (v/v) concentrations using the ideal gas law. The calibration range used encompassed 10 to 1,000 ppm (v/v).

Comparative Examples (controls) were prepared by dispensing a certain volume (5 mL) of the headspace of a 22 mL headspace vial containing about 5 grams of the noted contaminant analytes into an empty 22 mL headspace vial and quickly capping with a Teflon lined septum. The contaminant 1-butanol analytes were done with 0.5 and 5 mL spikes.

The Examples were prepared by adding the same volume of the noted contaminant that was added to the controls to an empty 22 mL headspace vial already containing the mass noted in TABLE 1 of the plurality of non-film forming polymer abatement particles ("Particles") (a styrene/acrylate, volatile base-swollen, crosslinked hollow sphere polymer powder available from The Dow Chemical Company as SunSpheres™ powder).

The Comparative Examples (controls) and the Examples were run via headspace GC-MS near room temperature (35° C., 10 min) and then the headspace of each was injected into the hot inlet of the GC-MS with the instrument settings noted above (about 2 hours after dispensing the noted contaminant analytes into the vials). The ppm volume/volume (v/v) concentration of the noted contaminant analytes in the headspace of each Comparative Example (control) and Example was then determined using the linear-least-squares equation from the calibration plot for the subject contaminant analyte (peak area vs. v/v concentration). The abatement performance of the Particles was calculated as the percent of contaminant analyte extracted by the Particles in the Example vials versus the Comparative Example (controls). The results are reported in TABLE 1.

TABLE 1

| Ex. | Particles (mg) | Analyte Contaminant | ppm (v/v) | Abatement (%) |
|---|---|---|---|---|
| C1 | — | 3-octanone | 130 | — |
| 1 | 13.00 | 3-octanone | 3 | 97.7 |
| C2 | — | 3-octanone | 127 | — |
| 2 | 10.01 | 3-octanone | 6 | 96.0 |
| C3 | — | 3-octanone | 193 | — |
| 3 | 50.84 | 3-octanone | 0.5 | 99.7 |
| C4 | — | 3-octanone | 137 | — |
| 4 | 49.21 | 3-octanone | 0.5 | 99.6 |
| C5 | — | d-limonene | 121 | — |
| 5a | 10.11 | d-limonene | 72 | 40.2 |
| 5b | 10.23 | d-limonene | 57 | 52.6 |
| 5c | 49.5 | d-limonene | 18 | 85.2 |
| 5d | 52.87 | d-limonene | 16 | 86.6 |
| C6 | — | 1-butanol | 220 | — |
| 6 | 9.8 | 1-butanol | 82 | 56.8 |
| C7 | — | 1-butanol | 158 | — |
| 7 | 50.5 | 1-butanol | 22 | 88.3 |
| C8 | — | 1-butanol | 37 | — |
| 8 | 10 | 1-butanol | 11 | 72.8 |
| C9 | — | 1-butanol | 43 | — |
| 9 | 50.5 | 1-butanol | 3 | 91.6 |

We claim:

1. An air treatment article, comprising:
a semipermeable barrier and
a plurality of non-film forming polymer abatement particles; wherein the non-film forming polymer abatement particles provided are multi-staged particles comprising: a core polymer and at least one shell polymer; wherein the core polymer accounts for 1 to 25 wt % of the non-film forming polymer abatement particles; wherein the core polymer comprises, as polymerized monomer units, 50 to 100 wt %, based on the weight of the core polymer, of at least one type of monoethylenically unsaturated core monomer containing a single carboxylic acid group; wherein the at least one shell polymer comprises, as polymerized monomer units: 10 to 50 wt %, based on the weight of the at least one shell polymer, of at least one type of multiethylenically unsaturated shell monomer; and 50 to 90 wt %, based on the weight of the at least one shell polymer, of at least one type of monoethylenically unsaturated shell monomer; wherein the non-film forming polymer abatement particles provided each contain a central void, wherein the non-film forming polymer abatement particles provided have an average void fraction of 1 to 70 vol %;
wherein the semipermeable barrier is disposed between an air atmosphere and the non-film forming polymer abatement particles;
wherein the semipermeable barrier impedes passage therethrough by the non-film forming polymer abatement particles;
wherein the semipermeable barrier permits passage therethrough by a for-treatment air containing a contaminant such that the for-treatment air can make contact with the non-film forming polymer abatement particles;
wherein the non-film forming polymer abatement particles have an affinity for the contaminant, wherein the contaminant comprises at least one of acetaldehyde, d-limonene, an aromatic, a pyridine, a pyrazine, 1-octen-3-ol, 3-methylfuran, 2-pentanol, 2-hexanone, 2-heptanone, 3-octanone, 3-octanol, trans-2-octen-1-ol, cis-2-octen-1-ol, 1-octene, 2-pentanone, 2-nonanone, borneol, geosmin, 1-butanol, 3-methyl-1-butanol, 3-methyl-2-butanol and thujopsene; and
wherein the non-film forming polymer abatement particles are a free flowing powder.

2. The air treatment article of claim 1, wherein the air treatment article is a multicomponent fiber having a sheath/hollow cavity fiber configuration with a sheath and a hollow cavity; wherein the semipermeable barrier forms at least a portion of the sheath; and wherein the non-film forming polymer abatement particles are disposed within the hollow cavity.

3. The air treatment article of claim 2, wherein the core polymer comprises, as polymerized monomer units, 90 to 100 wt %, based on weight of the core polymer, of an acrylic acid monomer and a methacrylic acid monomer; wherein the at least one shell polymer comprises, as polymerized monomer units, 15 to 30 wt %, based on the weight of the at least one shell polymer, of the at least one type of multiethylenically unsaturated shell monomer; wherein the at least one type of multiethylenically unsaturated shell monomer includes divinyl benzene; wherein the at least one shell polymer comprises, as polymerized monomer units 70 to 85 wt %, based on the weight of the at least one shell polymer, of the at least one type of monoethylenically unsaturated shell monomer; wherein the at least one type of monoethylenically unsaturated shell monomer includes methacrylic acid, methyl methacrylate, butyl methacrylate, sodium styrene sulfonate and styrene.

4. The air treatment article of claim 2, wherein the air treatment article is a fabric incorporating the multicomponent fiber.

5. The air treatment article of claim 2, wherein the air treatment article is a textile product incorporating a fabric, wherein the fabric incorporates the multicomponent fiber.

6. The air treatment article of claim 5, wherein the textile product is selected from the group consisting of apparel, upholstery, carpeting, wall coverings, bedding, towels, gloves, rugs, floor mats, drapery, napery, bar runners, awnings, automotive headliners and filters.

7. An air treatment article, comprising:
a semipermeable barrier and
a plurality of non-film forming polymer abatement particles; wherein the non-film forming polymer abatement particles provided are multi-staged particles comprising: a core polymer and at least one shell polymer; wherein the core polymer accounts for 1 to 25 wt % of the non-film forming polymer abatement particles; wherein the core polymer comprises, as polymerized monomer units, 50 to 100 wt %, based on the weight of the core polymer, of at least one type of monoethylenically unsaturated core monomer containing a single carboxylic acid group; wherein the at least one shell polymer comprises, as polymerized monomer units: 10 to 50 wt %, based on the weight of the at least one shell polymer, of at least one type of multiethylenically unsaturated shell monomer; and 50 to 90 wt %, based on the weight of the at least one shell polymer, of at least one type of monoethylenically unsaturated shell monomer; wherein the non-film forming polymer abatement particles provided each contain a central void, wherein the non-film forming polymer abatement particles provided have an average void fraction of 1 to 70 vol %;
wherein the semipermeable barrier is selected from the group consisting of at least one of a screen, a mesh, a woven or non-woven substrate, an expanded metal and a membrane;

wherein the semipermeable barrier is disposed between an air atmosphere and the non-film forming polymer abatement particles;

wherein the semipermeable barrier impedes passage therethrough by the non-film forming polymer abatement particles;

wherein the semipermeable barrier permits passage therethrough by a for-treatment air containing a contaminant such that the for-treatment air can make contact with the non-film forming polymer abatement particles;

wherein the non-film forming polymer abatement particles have an affinity for the contaminant, wherein the contaminant comprises at least one of acetaldehyde, d-limonene, an aromatic, a pyridine, a pyrazine, 1-octen-3-ol, 3-methylfuran, 2-pentanol, 2-hexanone, 2-heptanone, 3-octanone, 3-octanol, trans-2-octen-1-ol, cis-2-octen-1-ol, 1-octene, 2-pentanone, 2-nonanone, borneol, geosmin, 1-butanol, 3-methyl-1-butanol, 3-methyl-2-butanol and thujopsene; and wherein the non-film forming polymer abatement particles are a free flowing powder.

8. The air treatment article of claim 7, wherein the non-film forming polymer abatement particles are subjectable to fluidization upon contact with the for treatment air.

9. The air treatment article of claim 7, wherein the semipermeable barrier comprises a plurality of fibers; and wherein the plurality of fibers form a thin woven or nonwoven mat.

* * * * *